United States Patent [19]

Apontoweil et al.

[11] Patent Number: 4,645,665
[45] Date of Patent: Feb. 24, 1987

[54] LIVE INFECTIOUS BRONCHITIS VACCINE FOR POULTRY

[75] Inventors: Peter Apontoweil, Leersum; Manfred M. Krasselt, De Bilt, both of Netherlands

[73] Assignee: Gist-Brocades N.V., Delft, Netherlands

[21] Appl. No.: 621,078

[22] Filed: Jun. 15, 1984

Related U.S. Application Data

[62] Division of Ser. No. 409,996, Aug. 20, 1982, Pat. No. 4,481,188.

[30] Foreign Application Priority Data

Aug. 28, 1981 [EP] European Pat. Off. ....... 81-200960.3

[51] Int. Cl.$^4$ ............................................. A61K 39/215
[52] U.S. Cl. ................................................................ 424/89
[58] Field of Search ............................................ 424/89

[56] References Cited

U.S. PATENT DOCUMENTS

| Re. 31,830 | 2/1985 | Apontoweil et al. | 424/89 |
| 4,357,320 | 11/1982 | Apontoweil et al. | 424/89 |
| 4,481,188 | 11/1984 | Apontoweil et al. | 424/89 |
| 4,505,892 | 3/1985 | Apontoweil et al. | 424/89 |

FOREIGN PATENT DOCUMENTS

| 0030063 | 6/1981 | European Pat. Off. |
| 0073547 | 3/1983 | European Pat. Off. |
| 0073856 | 3/1983 | European Pat. Off. |

Primary Examiner—Shep K. Rose
Attorney, Agent, or Firm—Bierman & Muserlian

[57] ABSTRACT

Infectious bronchitis vaccines for poultry derived from at least a virus strain of a novel serotype of the infectious-bronchitis virus (IBV), identified by the internal indication Gelderland. 901 and Brabant. 802, which have been deposited at the Czechoslovak National Collection of Type Cultures of the Institute of Hygiene and Epidemiology under the numbers CNCTC AO 17/81 and CNCTC AO 18/82 and at the Collection Nationale de Cultures de Microorganismes d'Institut Pasteur, under Nos. I-168 and I-202 and combined infectious-bronchitis vaccines derived from the IBV H. 120 or the IBV H. 52 of the Massachusetts type strain together with the novel before-mentioned virus strain; the infectious-bronchitis virus strain itself, and a process for preventing infectious-bronchitis in poultry by vaccination with a vaccine derived from the before-mentioned strains. Preferably, live infectious bronchitis vaccines are prepared, which contain a virus content of at least $10^{4.0}$ EID$_{50}$ per dosage of each of the virus strains after freeze drying.

7 Claims, 1 Drawing Figure

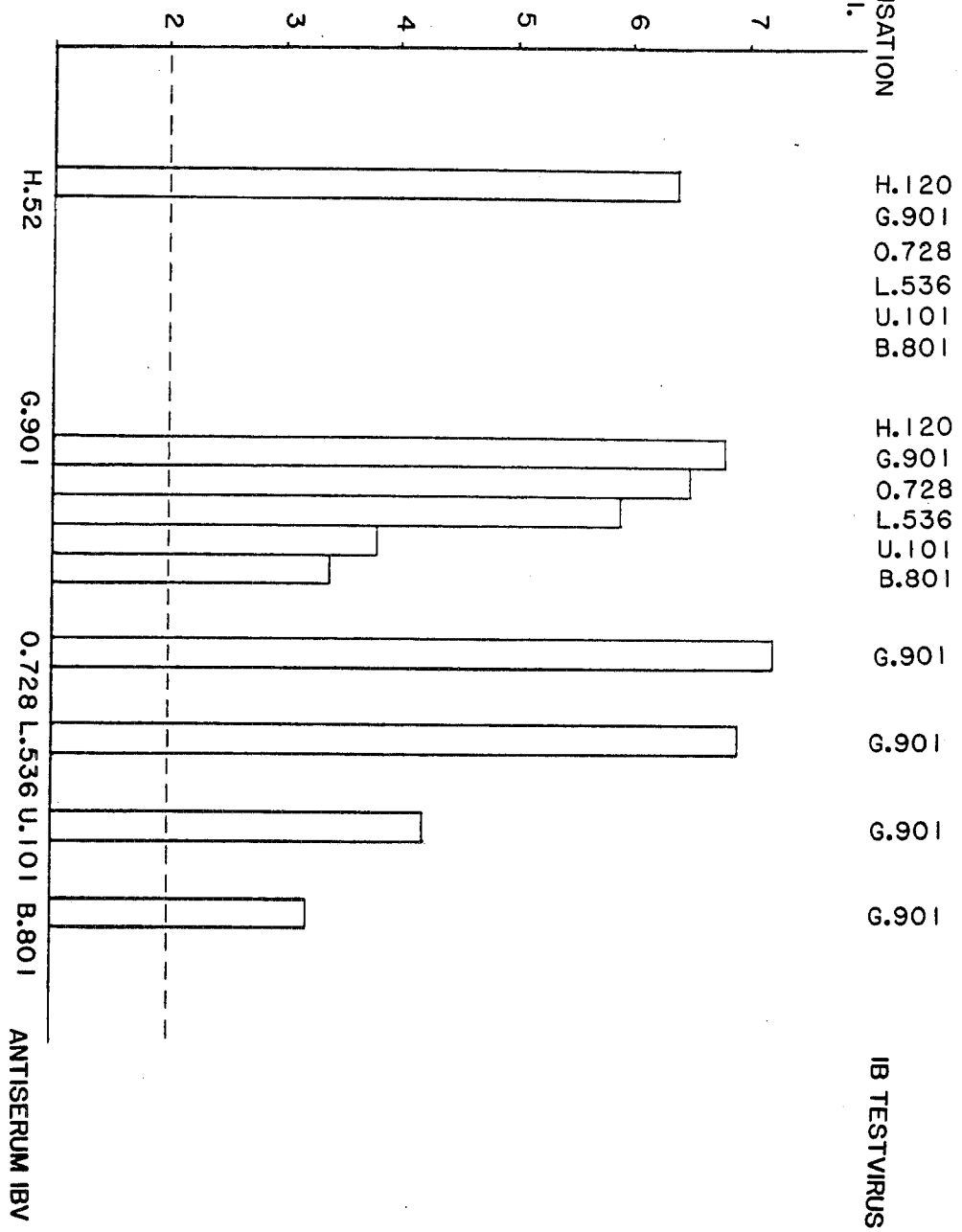

LIVE INFECTIOUS BRONCHITIS VACCINE FOR POULTRY

PRIOR APPLICATION

This application is a division of our copending commonly assigned U.S. patent application Ser. No. 409,996 filed Aug. 20, 1982, now U.S. Pat. No. 4,481,188.

STATE OF THE ART

The use of live infectious bronchitis vaccines for poultry has been known for many years and infectious bronchitis is an important affection of the respiratory system, the kidneys and oviduct of poultry. The cause of this syndrome is a corona virus and poultry are severely affected by epizootics of this disease. Infectious bronchitis causes a high mortality, especially in young poultry and besides mortality and more or less strong respiratory symptoms, egg production drops occur due to lesions to the oviduct and/or as as a result of the stress situation in which the poultry falls after an infection with IB virus. Moreover, infections with IB virus may stimulate latent virus- or bacterial infections and may give rise in this way to severe economical losses, especially in the broiler field.

To combat infectious bronchitis vaccines derived from inactivated virus as well as those derived from live virus are used. However, it was found that in some cases a loss of immunogenic properties occured after inactivation of these viruses with e.g. formaline and ultra violet light (M. S. Hofstad, Diseases of Poultry, Biester and Schwarte, Iowa University, Press. Ames. (1965), 615). As sound chickens can be killed or diseased by primary vaccination with live, non or slightly attenuated virus vaccines, whereby an especial danger exists for animals of less than 2 or 3 weeks old or for chickens shortly before the start or during laying. People skilled in this art have a clear preference for the application of dead vaccines which still have sufficient immunogenic properties, or of live vaccines which was tried to increase the harmlessness of such vaccines by means of attenuation of the original IB field virus isolates.

For such modified live virus vaccines, viruses having undergone 25 or more embryo passages to reduce their pathogenicity and their disseminating ability have been used up to now, such as viruses derived from the Massachusetts type and more particularly the IBV W 48, M 41 and 82828 strains of this type, besides the Connecticut isolates, e.g. the A 5968 strain. The immunizing capacity of these viruses is very specific against either Massachusetts or Connecticut types of IB virus. This is in contrast to the IBV H 52 and H 120 strains which have been passaged approximately 52 and 120 times respectively in embryonated chicken eggs and which have a relatively broad immunizing capacity. The H-strain is presently applied on a world wide scale because of its broad immunization spectre against among others Massachusetts and Connecticut types of IB-virus and has been isolated and attenuated by Bijlenga et al as disclosed in Tijdschr. Diergeneesk. 81:43, "Infectious bronchitis in chicks in the Netherlands" (1956), Tijdschr. Diergeneesk. 85:320 (1960), Tijdschr. Diergeneesk. 85:279 (1960) and Tijdschr. Diergeneeskunde 85:398 (1960).

Although the use of most vaccines of these modified strains has appeared to be fairly safe and effective up to now, these vaccines appear to be more and more unable to prevent outbreaks of infectious bronchitis in a sufficient manner under certain conditions as discussed in Avian Diseases, Vol. 20, No. 1, pages 42 and 177 (1976) and Avian Diseases, Vol. 19, No. 2, pages 323 and 583 (1975). This shortcoming of the present IB vaccines is attributed to occurring antigenic variations of the virus in an important degree, as appears e.g. from Archiv fur die Gesamte Virusforschung 34, p. 32 (1971) and Cunningham C. H. Develop. Biol. Standard, 33 p. 311 (1976).

Efforts were made therefore to reach an adequate vaccination of poultry by preparation and use of combined vaccines derived from IBV strains of different serotypes corresponding with the IBV types. However, a clearly encountered difficulty appeared to form the decrease of immunogenic properties of the respective starting viruses caused by mutual interaction as appears from Am. J. Vet. Res. 36, 4, 524 and 525 (1965) and Avian Diseases 12, 577 (1968).

The most adequate improvement which has been obtained up to now against the present frequently occuring IB virus infections caused by viruses deviating from the ones which can be combatted with vaccines derived from the H-strain, was obtained by the preparation and use of combined vaccines derived from one or more of the IV viruses identified as Utrecht. 101, Utrecht. 102, Drente. 201, Limburg. 501, Limburg. 502, Brabant. 801, Limburg. 536, Overijssel. 728 and Utrecht. 121, as disclosed in the European patent application No. 0 030 063. However, there is still existing need for further improved IB vaccines with immunizing properties over a wider range and/or better immunogenic properties.

It will be appreciated that the pursed improvement of these vaccines is still severely hampered by the appearance of new serotypes of IB-viruses, the change of immunogenic and other properties of the presently available IB viruses after a large number of passages in embryonated chicken eggs and the lack of sufficiently effectively applicable serological and immunological test procedures. In this connection reference may be made to Avian Diseases, Vol. 19 No. 12, page 323 and 324 (1975).

As a result of extensive research and experimentation, novel IB viruses could surprisingly be obtained and determined, which deviate from the frequently applied IB viruses of the H type (e.g. IB H 120 and IB H 52), but show corresponding antigenic properties with the viruses described in the beforementioned European patent application. The frequently used IB viruses of the H-type deviates from new IB virus in cross neutralization tests (virus neutralization tests) according to e.g. the method as described in American Association of Avian Pathologists, "Isolation and identification of Avian Pathogens", page 184 (1975), in the understanding that antisera diluted in a ratio of 1:5 are used, and in challenge experiments with subsequent virus reisolation tests. In other words, at an inoculation with a virus of the H-type (e.g. IB H 120 and IB H 52), the concerning animals are not protected against virus replication in the mucosa of the respiratory system after a challenge with one of the beforementioned deviating novel IB viruses. Antibodies against the IB H-strain equally appeared not to be able to neutralize significant amounts of IB virus of the novel deviating type.

Of special importance for the practice is that the novel IB virus causes respiratory symptoms with animals showing high antibody titers against the IB H- strain, and with still laying animals, egg production drops.

Each of the new IB virus generates after inoculation antibodies against not only itself, but also against the IB viruses different from the H-type strains, as mentioned in the above-cited European patent application. The new IB viruses therefore show a broad spectrum against the nowadays frequently occuring IB virus strains deviating from the ones which can be combatted with vaccines derived from the H-strain.

OBJECTS OF THE INVENTION

It is an object of the invention to provide novel infectious bronchitis viruses and vaccines prepared from the said viruses.

It is another object of the invention to provide novel combined infectious bronchitis vaccines and to novel processes for the preparation of the single or combined vaccines of the invention.

It is an additional object of the invention to provide novel methods of protecting poultry from infectious bronchitis.

These and other objects and advantages of the invention will become obvious from the following detailed description.

THE INVENTION

The novel infectious virus strains of the invention are novel serotypes of virus strain identified by the internal No. Brabant 802 and is deposited at the Czechoslovak National Collection of Type Cultures of the Institute of Hygiene and Epidemiology in Prague under No. CNCTC 18/82 and deposited at the Collection of Nationale d'Institute Pasteur, Paris under No. I-202 and a virus strain identified by the internal No. Gelderland 901 and is deposited at the Czechoslovak National Collection of Type Cultures of the Institute of Hygiene and Epidemiology in Prague under No. CNCTC AO 17/81 and deposited at the Collection Nationale de Cultures de Microorganismes d' Institute Pasteur, Paris under No. I-168.

These viruses were isolated by means of the trachea swab method from broiler chickens which showed at an age of 4–5 weeks respiratory symptoms after previous vaccination at the age of one day with IB vaccine of the H 120 type, whereby the animals found themselves at the moment of isolation in the district, which was indicated in the hereinbefore used internal notation (Gelderland and Brabant respectively). It was found that by attenuation to SPF-chicken embryos, the isolated virus strains lost their pathogenicity for SPF chickens to a major degree, in spite of the fact that its immunizing ability still remained present.

The virus strains with internal notation IBV Gelderland 901 (G. 901) and Brabant. 802 (B. 802) and deposited under Nos. CNCTC AO 17/81 and CNCTC AO 18/82 respectively and Nos. I-168 and I-202 respectively, showed these beforementioned characteristics after about 13, 45 and 90 SPF type I chicken embryo passages.

There was surprisingly found during a comparison test using conventional H 120 or H 52 vaccines that the protection against IB viruses of the Massachusetts type, measured as the amount of virus neutralizing antibodies, had not been diminished to a significant degree, if a H-type vaccine combined with the novel IBV isolate Gelderland. 901 or the IBV isolate Brabant. 802 was administered instead of the H-type vaccine alone. During this experimentation, one started from intranasal application of the concerning vaccines.

Cross neutralization tests in SPF chicken embryos and cross infection tests on SPF chickens were carried out giving results as shown in the following Tables 1, 2 and 3 and in FIG. 1. A neutralization index$>$2.0 means that the chickens involved were protected against the specific IBV infection.

TABLE 1

Cross neutralization test in SPF chicken embryos.

| Infectious bronchitis testvirus | Neutralization index (N.I.) with antiserum against infectious bronchitis virus | | | | |
|---|---|---|---|---|---|
| | H.52 | G.901 | O.728 | L.536 | U.101 |
| H.120 | 6.4 | 1.6 | 0.3 | 0.4 | 1.9 |
| G.901 | 0.8 | 6.8 | 7.2 | 6.9 | 4.2 |
| O.728 | ND | 6.5 | ND | ND | ND |
| L.536 | ND | 4,9 | ND | ND | ND |
| U.101 | ND | 3,8 | ND | ND | ND |

The abbreviation "ND" means "not done"

TABLE 2

Cross neutralization tests in SPF chicken embryos.

| Infectious bronchitis testvirus | Neutralization index (NI) with antiserum against infectious bronchitis virus | | | | |
|---|---|---|---|---|---|
| | H.52 | O.728 | L.536 | U.101 | B.801 |
| B.802 | 0.4 | 3.6 | 2.1 | 2.8 | 3.3 |

TABLE 3

Cross infection tests with 4 week old SPF chickens.

| Vaccine virus | Challenge virus | Virus reisolation |
|---|---|---|
| IBV G.901 | IBV G.901 | 0/5 positive |
| | IBV VOET (Massachusetts) | 3/5 positive |
| | IBV O.728 | 0/5 positive |
| IBV H.120 | IBV G.901 | 4/5 positive |
| | IBV VOET (Massachusetts) | 0/5 positive |
| | IBV 0.728 | 5/5 positive |

The vaccine virus was administered intranasally at a dose of $10^{4\cdot0}$ $EID_{50}$ per bird.

The virus reisolation test was carried out 5 days after challenge using trachea swab material and the virus reisolation technique used is described in "Specifications for the production and control of avian live virus vaccines" of the Ministry of Agriculture, Fisheries and Food of the United Kindom Central Veterinary Laboratory of Biological Products and Standards Department, New Haw, Weybridge, Surrey KT153 NB, 2nd Edition (1977), p. 12.

From the results of Tables 1, 2 and 3 (cross neutralization and cross infection tests), it appears that the applied serotype of the novel IBV G. 901 and IBV B. 802 differs anti-genitically from the H-strain and, having in mind the results of the challenge experiments with additional virus reisolation, shows attractive immunogenic properties as to the homologeous viruses as described in the above-mentioned European Patent Application. Field experiments showed that in sera of broilers, reproduction chickens and laying hens, antibodies were frequently occurring against the virus type Gelderland. 901 and Brabant. 802.

In FIG. 1 the neutralization indices (vertical axis) determined for the IBV test viruses H. 120, Gelderland. 901, Overijssel. 728, Limburg. 536, Utrecht. 101 and Brabant. 801 respectively and for the homologeous test virus Gelderland. 901, are plotted for the six IBV anti sera types H. 52, Gelderland.901, Overijssel. 728, Limburg. 536, Utrecht. 101 and Brabant. 801 on the horizontal axis. It will be appreciated therefore that the novel IB virus strains differs antigenitically in a significant degree from the usually applied H-virus and have common antigenic properties with the viruses of the beforementioned European application.

The novel isolated virus strains could be characterized by the following tests:

Chloroform treatment according to Mayr, et al, Virologische Arbeitsmethoden, G. Fischer Verlag, Jena, 1977, p. 285 of infectious amnion allantoic fluid obtained by cultivation of original virus containing samples from infected homogenized organ and trachea swab material in the allantoic cavity of 10 days preincubated SPF chicken eggs, resulted, in comparison with the untreated material, in a reduction of virus content from $10^{7.5}$ to $10^{1.5}$ EID$_{50}$. This experience points to the presence of a virus agent which contains in his envelope a lipid which is necessary for the infectivity. The infectious amnion-allantoic fluid caused no agglutination with erythrocytes derived from SPF chickens.

Addition of 5-fluorodesoxyuridine (FUDR) to the culture medium of chicken kidney cell cultures serving for replication of the agent did not influence the intracellular synthesis of the virus agent to a significant degree.

The EID$_{50}$ content of the cell material and culture medium appeared to reside on comparable levels 2, 4 and 7 days after the inoculation of the virus agent, i.e. the nucleic acid to be replicated belongs to the group of the ribonucleic acid.

Examination with electron microscope showed that the virus agent present in the amnion allantoic fluid harvested within 30 hours after the artificial infection possessed a diameter of about 100 nm. About 15 nm long projections were present on the surface of this virus and the virus has the size and shape of a corona virus to which also the avian bronchitis viruses are regarded to belong.

It will be appreciated that the properties of the novel serotype of the IB-viruses of the present invention make the novel virus strains especially suitable for the preparation of as well inactivated as live poultry vaccines on behalf of a more efficient protection against infectious bronchitis, especially in areas of countries wherein the described deviating serotype of the present application and the above-mentioned European patent application occur besides the IB viruses of the so called H-type.

More particularly, virus strains of the serotypes of the hereinbefore mentioned novel virus strains may successfully be used for the preparation of mixed live and inactivated vaccines derived as well from the novel IB strain as from the H-strain. It will be appreciated that novel IB vaccines of the present invention may be derived from the beforementioned novel strains G. 901 and B. 802 and mutants or variants thereof belonging to the same serotype.

The novel IBV vaccines of the present invention may be obtained by propagation of the novel virus strains by methods known in the art in principle and optionally followed by inactivation by methods known in the art in principle. For instance, the virus may be propagated in embryonated SPF chicken eggs or in suitable cell cultures such as chicken kidney cell cultures. However, with such a process, it has to be checked that the antigenic properties and the degree of virus replication do not significantly change. Then, the cultivated virus material is collected and purified and finally one or more stabilizers and, if desired, antibiotics such as sodium penicillin G, streptomycin or natamycin may be added and the mixture is lyophilized.

More particularly, the seed virus concerned is inoculated under sterile conditions into the allantoic cavity of 10-11 days preincubated SPF type I chicken eggs. After incubation for 28 to 48 hours at 37° C., the amnion-allantoic fluid of the then still living and of the specifically dead (i.e. between 24 hours after the seed virus inoculation and the end of the incubation period) embryos is harvested, purified and lyophilized after optional addition of stabilizers and/or antibiotics.

According to this process, single vaccines can be prepared containing the virus in an amount of at least $10^{4.0}$ EID$_{50}$ per dose after lyophilization, while e.g. so prepared combined vaccines of one of the novel virus strain and a known H-strain and/or more other IBV-strains showed a virus content of $\geq 2 \times 10^{4.0}$ EID$_{50}$ per dose and preferably a content of each of the virus components of at least $10^{4.0}$ EID$_{50}$ per dose.

It will be appreciated that the present invention also relates to novel, inactivated as well as live, IBV vaccines which have been at least derived from one virus belonging to one of the serotypes of the novel IB virus strains G.901 and B.802 and to the use of such vaccines to protect poultry.

Preferably live vaccines derived from viruses of the serotypes of the novel virus G.901 or from the novel virus B.208 alone or from the H-type virus with the novel IB-virus are used. More preferably, live vaccines derived from H 120 or H 52 virus strain from viruses of the serotype of the G.901 virus strain or from the B.802, virus strain are used. The vaccines may also be administered to young chickens.

The novel live virus vaccines may be administered by the so called eyedrop- or nosedrop-, the drinking-water- or spray methods. Vaccination of the novel live vaccines of the invention preferably is carried out with poultry of an age of 1 day to 18 weeks. The novel inactivated vaccines may be administered to the birds subcutaneously or intramuscularly and may be used for revaccination purposes only.

As examples of suitable inactivated combination vaccines as indicated hereinbefore may be mentioned those derived from the strains G.901, B.801 and H.52, derived from the strains B.802, L.536 and H.52, derived from the strains G.901, B.802, B.801 and H.52 respectively. It will be appreciated that also combined live or inactivated vaccines derived from the novel IB strain type G.901 or B.802 and one or more completely other virus types such as e.g. the Newcastle disease virus, adeno-like virus, infectious bursitus virus or reo virus, are a feature of the present invention too.

For the preparation of inactivated IBV vaccines of the invention, there may be started from e.g. an amnionallantoic fluid which may be diluted with PBS and to which a suitable carrier is added after inactivation by methods known in the art, e.g. by means of beta-propiolactone or formaline. Preferably, the virus suspension with a suitable virus content is processed to a water-in-oil emulsion vaccine derived from a mineral or plant oil and one or more emulsifiers such as non-ionic surface-active compounds derived from alkylene oxide and/or hexahydric alcohols and/or higher natural fatty acids ($C_{10}$–$C_{20}$) such as esters or esterethers. Examples of the last mentioned emulsifiers are sorbitan or mannide monooleate (Span 80 ®, Arlacel 80 ®, Arlacel A ®) and polyoxyethylene (20) sorbitan monooleate (e.g. Tween 80 ®). The volume ratio between the aqueous phase (virus fluid) and the oily phase may vary from 3:7 to 1:1 and lies preferably at a ratio of about 7:13.

In the following examples there are described several preferred embodiments to illustrate the invention. However, it should be understood that the invention is not intended to be limited to specific embodiments.

EXAMPLE 1

Preparation of live IB virus vaccine of the strain G.901

STEP A: Cultivation of virus

Type I SPF chicken egg preincubated for 10 to 11 days were inoculated into the allantoic cavity with $10^{3.0}$ to $10^{4.0}$ $EID_{50}$ IBV G.901 seed virus (0.2 ml per egg) and the eggs were candled for the first time 20 to 24 hous after the virus inoculation and all aspecifically dead embryos were removed. After an incubation period of in total 28 hours at $+37°$ C., the amnion-allantoic fluid (AAF) was harvested.

STEP B: Treatment of virus suspension

After purification of the AAF by centrifugation for 20 minutes at 2000 r.p.m. in a cooling centrifuge and/or by filtration, $5 \times 10^5$ units of sodium penicillin G and 800 mg of streptomycin per liter were added to the AAF. The virus material was subsequently stabilized by addition of at least 3% by weight of albumin and/or mannitol and the stabilized bulk virus material was frozen to at least $-35°$ C. and stored at such temperature until the further processing phase.

Samples of this material were tested for their virus content by the $EID_{50}$ (Egg Infectious Dose 50%) assay method. After the test results were available, the virus material was thawed and filled into lyophilization flasks. The virus content (volume) was adjusted in such a way that at the end of the subsequent lyophilization there were still at least $10^{4.0}$ $EID_{50}$ of the concerning virus per dose present in the vaccine. The flasks were sealed under vacuum at the end of the lyophilization process.

EXAMPLE 2

Preparation of a combined live IB virus vaccine of the strain H.52 and G.901

With the preparation of the multivalent (combined) vaccine, care has to be taken so that the minimum virus contents for all virus components reached.

STEP A: Cultivation of virus

Type I SPF chicken eggs which had been preincubated for 10 to 11 days were inoculated into the allantoic cavity with $10^{3.0}$ to $10^{4.0}$ $EID_{50}$ of H.52 or G.901 seed virus (0.2 ml in total per egg) and the eggs were candled for the first time 20 to 24 hours after the virus inoculation. All aspecifically dead embryos were removed and after an incubation period of a total 32 hours at 37° C., the AAF was harvested.

STEP B: Treatment of the virus suspension

After purification of the AAF by centrifugation for 20 minutes at 2000 r.p.m. in a cooling centrifuge and/or by filtration, $8 \times 10^5$ units of sodium penicillin G and 1000 mg of streptomycin per liter were added to the AAF. The virus material was subsequently stabilized by addition of at least 3% by weight of albumin and/or mannitol and the stabilized bulk virus material was then frozen to at least $-35°$ C. and kept at this temperature until further processing.

Meanwhile, samples of this material were tested for their virus content by the $EID_{50}$ assay method. The virus material was thawed and filled out into lyophilization flasks after the test results were available. The virus content (volume) was adjusted in such a way that at the end of the lyophilization process, the vaccine contained per dose at least $10^{4.0}$ $EID_{50}$ of each virus concerned. The flasks were sealed under vacuo at the end of the lyophilization process. During the preparation of the multivalent (combined) vaccine, care had to be taken that the minimum virus content for all virus components were reached.

EXAMPLE 3

Preparation of inactivated combined IB-virus vaccine of the strains H 52 and G.901

In a manner similar to Example 2A, the virus was cultivated in SPF eggs and the obtained virus suspension was treated in a similar way as in Example 2B until the frozen phase was reached but without addition of antibiotics and stabilizers. The frozenk AAF was thawed and inactivated in a water bath by 0.1% of beta-propiolactone for a period of 90 minutes at 37° C. Then, the virus suspension was kept overnight at $+4°$ C. and the inactivation was checked by inoculation of preincubated, embryonated SPF chicken eggs with the inactivated virus material and subsequent incubation.

The AAF's of strain H.52 and of strain G.901 were mixed in a ratio of 3:2 and the mixed inactivated AAF was diluted, if necessary, with PBS+0.3% of formaline depending on the virus content of each virus type determined in the noninactivated AAF (to a concentration of at least $10^{7.0}$ $EID_{50}$ per ml for all virus strains). 3.5% of Tween 80 were added to the virus suspension of the two strains and the inactivated virus suspension was mixed with an oil phase in the ratio of 6.5 parts of oil to 3.5 parts of virus fluid and emulsified so that the average particle size of the aqueous phase was about $0.5\mu$.

The emulsification was carried out with an Ultra Turrax homogenizer or by passing the starting mixture through a colloid mill. The oil phase had the following composition: Marcol 5 2 ® (white paraffinic Esso oil) 93.5% Arlacel A ®, Arlacel 80 ® or Span 80 ® (mannide monooleate).

The components of the oil phase were separately heated to 110° C. in an autoclave or the mixture was sterilized by filtration.

EXAMPLE 4

Preparation of inactivated combined IB-virus vaccine of the strains H 52, G. 901 and B. 801

The B.801 virus and the G.901 virus were cultivated in SPF eggs in the same way as described in Example 1 for the G.901 virus strain and H. 52 virus containing AAF was prepared in the same way as in Example 2. The treatment of the virus suspensions of the three strains was carried out according to the corresponding steps of Example 3 until the inactivated AAF's were mixed. The inactivated AAF of strain H.52 was then mixed with the AAF of strain G.901 and of strain B.801 in the ratio of 8:3:3. The mixed inactivated AAF was diluted, if necessary, with PBS+0.3% of formaline depending on the virus content of each virus type determined in the non-inactivated AAF (at least $10^{7.0}$ $EID_{50}$ per ml for all virus strains).

2.6% of Tween 80 were added to the virus suspension of the three strains and the inactivated virus suspension was mixed with an oil phase in the ratio of 6.0 parts of oil to 4.0 parts of virus fluid and emulsified so that the average particle size of the aqueous phase was about 0.5μ. The emulsification was carried out with an Ultra Turrax homogenizer or by passing the starting mixture through a colloid mill. The composition of the oil phase was the same as in Example 3.

EXAMPLE 5

Preparation of live IB virus-vaccine of strain B.802

Cultivation of virus and treatment of the virus suspension was carried out according to the corresponding steps of Example 1, but AAF was harvested after an incubation period of 32 hours at 37° C. instead of 28 hours.

EXAMPLE 6

Preparation of inactivated combined IB-virus vaccine of the strains H.52, B.802 and L.536

The B.802 virus and L.536 virus were cultivated in SPF eggs in the same way as described in Example 1 for the G.901 virus, but an incubation period of 32 hours was taken before AAF was harvested. H.52 virus was cultivated in the same way as in Example 2 and the treatment of virus suspensions of the three strains was carried out according to the corresponding steps in Example 4. The inactivated AAF's of strain H.52, strain B. 802 and strain L.356 were mixed in the ratio 3:1:1 and further treatment and emulsification was carried out as described in Example 4.

EXAMPLE 7

Preparation of inactivated combined IB-virus vaccine of the strains H.52, B.802 and G.901

The B.802 virus and G.901 virus were cultivated in SPF eggs in the same way as described in Example 1 for the G.901 virus, but an incubation period of 32 hours was taken before AAF was harvested and H.52 virus was cultivated in the same way as in Example 2. The treatment of the virus suspensions of the three strains was carried out according to the corresponding steps in Example 4 and the inactivated AAF's of strain H.52, strain B.802 and strain G.901 were mixed in the ratio 3:1:1. Further treatment and emulsification was carried out as described in Example 4.

Various modifications of the products and processes of the invention may be made without departing from the spirit or scope thereof and it is to be understood that the invention is to be limited only as defined in the appended claims.

What we claim is:

1. A live infectious bronchitis vaccine for poultry characterized in that it is derived from at least one virus strain selected from the group consisting of serotype of the virus strain identified by means of the internal notation Gelderland. 901 deposited at the Czechoslovak National Collection of Type Cultures of the Institute of Hygiene and Epid emiology in Prague Under No. CNCTC AO 17/81 and deposited at the Collection Nationale de Cultures de Micro organismes d'Institute Pasteur, Paris, under No. I-168 and novel serotype of the virus strain identified by means of the internal notation Brabant. 802, deposited at the Czechoslovak National Collection of Type Cultures of the Institute of Hygiene and Epidemiology in Prague under No. CNCTC. 18/82 and deposited at the Collection National d'Institute Pasteur, Paris, under I-202 and a vaccine carrier, the vaccine having after lyophillization, a virus content of at least $10^{4.0}$ EID$_{50}$ of each of the virus strains per dose.

2. A combined infectious bronchitis vaccine of a vaccine of claim 1 combined with a second vaccine derived from the IBV H120 or the IBV H52 of the Massachusetts type.

3. An infectious bronchitis vaccines of claim 2 wherein the second vaccine is derived from the IBV H 52 of the Massachusette type.

4. A live infectious bronchitis vaccine of claim 1 having after lyophilization, a total virus content of at least $2 \times 10^{4.0}$ EID$_{50}$ of the virus strains per dose.

5. A method of protecting poultry against infectious bronchitis comprising vaccinating poultry with an amount of a vaccine of claim 1 sufficient to protect the poultry against infectious bronchitis.

6. The method of claim 5 wherein the vaccine is a combined vaccine with a second vaccine derived from the IBV H 120 or IBV H 52 of the Massachusetts type.

7. The method of claim 5 wherein the second vaccine of IBV H 52 of the Massachusetts type.

* * * * *